United States Patent [19]

Nonomura

[11] Patent Number: 4,713,398

[45] Date of Patent: Dec. 15, 1987

[54] NATURALLY-DERIVED CAROTENE/OIL COMPOSITION

[75] Inventor: Arthur M. Nonomura, Del Mar, Calif.

[73] Assignee: Microbio Resources, Inc., San Diego, Calif.

[21] Appl. No.: 771,401

[22] Filed: Aug. 30, 1985

[51] Int. Cl.$^4$ ..................... A61K 31/07; A61K 31/40; A61K 31/355

[52] U.S. Cl. .................................. 514/725; 514/410; 514/458; 514/937

[58] Field of Search ..................... 424/195.1; 514/763, 514/725, 458, 937

[56] References Cited

U.S. PATENT DOCUMENTS

| | | | |
|---|---|---|---|
| 2,949,700 | 8/1960 | Kathrein | 435/67 |
| 3,920,834 | 11/1975 | Klaui et al. | 514/763 |
| 4,115,949 | 9/1978 | Avron et al. | 568/869 |
| 4,435,927 | 3/1984 | Hoppe et al. | 514/763 |

OTHER PUBLICATIONS

Merck Index 9th Ed. 1976, Nos. 1852–1855 pp. 236–237.

*Primary Examiner*—J. R. Brown
*Assistant Examiner*—John W. Rollins
*Attorney, Agent, or Firm*—Brown, Martin, Haller & Meador

[57] ABSTRACT

A composition is described comprising naturally-derived carotene dispersed in a non-petroleum, naturally-derived edible oil. The carotene may be in form of its mixed isomers, or one or more of the individual isomers may be present to the exclusion of the others. Of the isomers the beta-carotene isomer is preferred, although others, notably the alpha- and gamma-carotene isomers, are also desirable components. Naturally-derived stabilizers may be present in the composition. The carotene content is 0.5–7.5 weight percent of the composition. The carotene is preferably obtained from algae. No petro-chemical residues are present in the composition since the formulation is produced at all stages without use of petrochemical contact.

16 Claims, No Drawings

NATURALLY-DERIVED CAROTENE/OIL COMPOSITION

FIELD OF THE INVENTION

This invention relates to carotene/oil compositions, particularly those containing beta-carotene.

BACKGROUND OF THE INVENTION

Retinol (Vitamin A) is known to be necessary to the biochemistry of human vision. Through a series of reactions the retinol is converted through retinal isomers to rhodopsin ("visual purple"). Irradiation of the rhodopsin with visible light in turn causes a series of isomerization reactions through the retinal isomers to opsin resulting in excitation of the retinal rod cells and generation of a visual nerve impulse. A deficiency of Vitamin A in the system leads to reduced visual sensitivity (especially night blindness) and in extreme cases (e.g., keratomalacia or xerophthalmia) to complete blindness.

Vitamin A is also known to be necessary to the proper function of the epithelial tissues. Deficiency of Vitamin A in such cases results in disorders such as reduced resistance to infection through epithelial surfaces.

Increases in the level of Vitamin A in the body may to some extent be obtained by administering doses of Vitamin A directly to an individual. However, there is a limited bodily tolerance to Vitamin A, and overdoses of Vitamin A can lead to toxic effects. Since the tolerance level varies widely among individuals, it is not generally advisable to administer substantial doses of Vitamin A except under carefully controlled circumstances.

It is well known that carotene is the precursor of Vitamin A. (There are several carotene isomers, including the alpha-, beta- and gamma-carotene isomers. Of these the beta-carotene isomer has the most Vitamin A activity and is also the most common. As used herein, the terms "carotene" or "the carotenes" will refer to mixtures of two ormore of the isomers or to an individual isomer as appropriate tothe context. If a particular isomer is of specific importance to a particular context, it will be so identified.) The carotenes are oxidized by liver enzymes to produce Vitamin A. Significantly, however, the enzyme metabolism produces only the amount of Vitamin a that can be utilized by the body; it does not produce an overdose of Vitamin A. Consequently, an individual can be administered doses of carotene in quantities large enough to produce optimum levels of Vitamin A in the body without the risk of a toxic Vitamin A reaction. Excess carotene which is administered is stored in fatty tissues and organs.

The carotenes, particularly beta-carotene, are present in many common foods, primarily the green and yellow vegetables such as tomatoes, citrus fruits, carrots, squash, turnips, broccoli and spinach. The concentration of carotene in these vegetables is relatively low, and a person must consume substantial quantities of the vegetables to have a high intake level of carotene. The normal diet for most people does not include such large quantities of these vegetables, so there has developed a commercial market for concentrated carotene dietary supplements, particularly those in which the carotene is beta-carotene because of its high Vitamin A activity. These supplements normally have been produced by extraction of carotene from vegetables such as carrots by use of petrochemical solvents. The resulting carotene, usually in crystalline form, can be expected to be associated with at least residual quantities of such solvents. This is particularly true when the carotene is administered in a dosage form in which it is dispersed in a petrochemical or other "synthetic" oil. The presence, even in minute quantities, of such petrochemical residues in the carotene supplements has caused apprehension among users of the supplements.

It is also known that certain algae, especially those in the classes Rhodophyta (red algae) and Chlorophyta (green algae), are good sources of carotene. The carotene content of species of the genus Dunaliella have been reported in U.S. Pats. Nos. 4,115,949 and 4,119,895 and in *Acta Chem. Scand.* 23, 7, 2544–2545 (1979). Similar data for the genus Chlorococcum has been disclosed in U.S. Pat. No. 2,949,700. In the past, however, all extraction processes to produce the carotene from algae have involved the use of petrochemical solvents, which results in the same contamination problems discussed above for the vegetable extractions. In addition, many of the algal extraction processes have involved drying of the alga, which has been found to degrade the carotene.

In addition to the use of carotene as a precursor for Vitamin A, there have recently been reports in the literature tha suggest that carotene is itself useful in the prevention of certain types of cancers which are believed to be promoted by oxidizing free radicals. It is postulated that carotene, which has an affinity for such free radicals, may serve to reduce the free radical level in the body, thereby reducing the occurrence of free radical initiation of malignancies. There are studies currently underway which are expected to provide more information regarding the effects of carotene on such cancers.

It would therefore be of benefit to have carotene available in a form which would be safe and therapeutically useful for humans, and which would not result in petrochemical contamination of the carotene.

BRIEF SUMMARY OF THE INVENTION

The invention herein is a composition comprising naturally-derived carotene dispersed in a non-petroleum, naturally-derived, edible oil.

Embodiments of the invention are further characterized by inclusion in the composition of individual specific isomers of carotene, including the alpha- and gamma-carotene isomers, and especially the beta-carotene isomer, as well as chlorophylls such as phaeophytin; low crystalline carotene content and the incorporation if desired of stabilizers.

In a particularly preferred embodiment the carotene is initially obtained from algae.

The carotene content in the oil medium is from 0.5–7.5% by weight.

DETAILED DESCRIPTION OF THE INVENTION

For the purpose of this invention the term "naturally derived" means that the components of the composition as well as the raw materials from which these components are obtained have not previously been grown in or treated with petrochemical materials such a petrochemical solvents. It also means that the initial sources of the raw materials or the components are not petrochemicals. The carotenes and the various vegetable oils are of course naturally occurring materials, but the term "natural" has unfortunately frequently been misused in the commercial vitamin supplement field in the past few years. Products are labeled "natural" although they have been produced with, treated by or combined with synthetic or petrochemical chemicals such as solvents. Thus while the principal active ingredient may be a naturally occurring material, the entire formulation used as the vitamin supplement contains significant and often predominant quantities of materials which are frequently not part of the human diet. Consequently, the term "naturally derived" is used herein to provide an appropriately precise definition.

The oil used in the present composition as the carrier medium may be any non-petroleum, naturally derived, edible oil. Of the animal and vegetable oils useful in this product most preferred are the vegetable oils such as corn oil, safflower oil, peanut oil, sunflower oil, coconut oil, sesame oil, soybean oil and various mixtures of these oils. Useful animal oils include the fish oils and lard oil. All of these may be produced from the animal and vegetable sources by known processes which do not utilize petrochemical solvents or intermediates. Various types of oil extraction and refinement processes are described in Shreve et al, *Chemical Process Industries,* (4th edn., 1977) in Chapter 28.

Carotene may be obtained from a variety of vegetable sources, including green and yellow vegetables such as carrots, spinach, broccoli, alfalfa and sweet potatoes and from algae of the classes Chlorophta (green algae) and, less frequently, Rhodophyta (red algae). Several processes have been described for extraction of carotene from vegetables or algae. Such processes to be useful in the present invention must of course be free of petrochemical components and treatments. As a particularly preferred extraction process, I have invented a process for directly extracting carotene from algae into the oil medium, which process I have claimed in a patent application filed simultaneously herewith and entitled PROCESS FOR PRODUCING A NATURALLY DERIVED CAROTENE/OIL COMPOSITION BY DIRECT EXTRACTION FROM ALGAE (Attorney's Docket No. MBR 001). It is preferred that the carotene be obtained by extraction from species of the alga Dunaliella which has substantial carotene content and which can be cultivated to increase the carotene content to high levels.

It is possible in some cases to produce a carotene/oil composition of this invention which contains only one carotene isomer, such as beta-carotene. From a more practical point of view, however, it is found that the carotene as derived from its raw material source, whether algae or common vegetables, normally is a mixture of carotene isomers and also contains chlorophyll or derivatives thereof. In a process such as my direct extraction process referred to above, the carotene is a mixture of the carotene isomers, with beta-carotene predominating (usually about 95% of the carotene content).

The carotene and oil may be blended in any suitable manner that will provide for good dispersion of the carotene uniformly through the oil medium. In my extraction process an oil/water emulsion in which the water slurry contains algae is homogenized and the carotene extracted directly from the algae into the minute oil droplets. When the emulsion is subsequently broken the carotene is in the oil phase. Other processes may proceed by forming carotene solids and then dissolving the solids in the oil.

The carotene content of the present composition will be from about 0.5-7.5 weight percent carotene, preferably from 1-5, more preferably 1-2, weight percent.

The degree of crystalline carotene content in the oil medium is believed to be of significance in the physiological utilization of this product. Specifically, it is believed that there may be enhanced effectiveness if the crystal content is kept low. The limit of solubility of the carotene in oil is about one percent concentration, so above that level some crystals form.

I have found that it is useful to incorporate a small amount of a naturally derived stabilizer into the carotene/oil composition. The stabilizer content should be no more than about 0.5 percent of the composition. A particularly useful stabilizer is a mixture of the tocopherol isomers (Vitamin E).

The composition of the present invention can be prepared in dosage form by encapsulating appropriate dosage quantities in gelatin capsules which are then taken orally by the user.

As a typical example of the composition of the present invention, carotene was extracted directly into corn oil according to the process of my copending application. The carotene content was 1.4 weight percent of the composition, of which only 5 percent of the carotene was crystalline. Mixed tocopherols at a 0.3 weight percent content were present as a stabilizer.

It will be evident that there are embodiments not described above which are clearly within the scope and spirit of the present invention. The above description is therefore intended to be exemplary and the scope of the invention is to be limited solely by the appended claims.

I claim:

1. A composition consisting essentially of naturally-derived carotene dispersed in a non-petroleum, naturally-derived edible oil, wherein said carotene is present as 1-5 weight percent of said composition.
2. A composition as in claim 1 wherein said carotene comprises a mixture of isomers of carotene.
3. A composition as in claim 2 wherein said isomers are selected from the group consisting of the alpha-, beta- and gamma- isomers of carotene.
4. A composition as in claim 3 wherein the carotene comprises the beta- isomer of carotene.
5. A composition as in claim 1 further comprising naturally-derived chlorophyll derivatives.
6. A composition as in claim 1 further containing a naturally-derived stabilizer.
7. A composition as in claim 6 wherein said stabilizer comprises mixed tocopherols.
8. A composition as in claim 1 wherein said carotene is obtained from algae.
9. A composition as in claim 8 wherein said algae are selected from carotene-containing members of the classes Chrlorophyta and Rhodophyta.
10. A composition as in claim 9 wherein said algae are selected from the class Chlorophyta.
11. A composition as in claim 10 wherein said algae are of the genus Dunaliella.
12. A composition as in claim 1 wherein said carotene is obtained from vegetables.
13. A composition as in claim 1 wherein said edible oil is an animal or vegetable oil.
14. A composition as in claim 13 wherein said oil is a vegetable oil.
15. A composition as in claim 14 wherein said vegetable oil is selected from the group consisting of corn oil, safflower oil, peanut oil, sunflower oil, coconut oil, sesame oil, soybean oil or mixtures thereof.
16. A composition as in claim 1 wherein said carotene is present as 1-2 weight percent of the composition.

* * * * *